United States Patent [19]
Flatland

[11] 3,962,789
[45] June 15, 1976

[54] DENTAL HANDPIECE

[76] Inventor: Lloyd P. Flatland, 15 Quisisana Drive, Kentfield, Calif. 94904

[22] Filed: Apr. 8, 1974

[21] Appl. No.: 458,792

[52] U.S. Cl. .................................. 32/27; 415/503
[51] Int. Cl.² ............................................ A61C 1/10
[58] Field of Search ............ 32/26, 27, 28; 308/132, 308/187 R; 184/55 A, 64, 6.26; 415/503, 213 T

[56] References Cited
UNITED STATES PATENTS

| | | | |
|---|---|---|---|
| 1,838,982 | 12/1931 | Angell | 32/27 |
| 2,439,910 | 4/1948 | Snyder | 184/55 A |
| 2,564,309 | 8/1951 | Norgren | 184/55 A |
| 2,792,073 | 5/1957 | Boss | 184/55 A |
| 2,842,062 | 7/1958 | Wright | 415/213 T |
| 3,197,869 | 8/1965 | Staunt | 184/55 A X |
| 3,261,426 | 7/1966 | Kuhlman | 184/55 A |
| 3,298,103 | 1/1967 | Maurer | 32/27 |
| 3,380,162 | 4/1968 | Heathe | 415/503 |
| 3,592,566 | 7/1971 | Beardslee | 415/213 T |
| 3,685,287 | 8/1972 | Dooley | 415/213 T |

FOREIGN PATENTS OR APPLICATIONS 107,059  10/1924  Switzerland ............... 415/213 T

*Primary Examiner*—Louis G. Mancene
*Assistant Examiner*—Jack Q. Lever
*Attorney, Agent, or Firm*—Lothrop & West

[57] ABSTRACT

An air driven dental handpiece has a housing defining a rotor chamber and also defining an inlet duct leading into the chamber as well as an outlet duct opening from the chamber. There is a spindle mounted in the housing for rotation in the chamber about an axis. A rotor in the chamber is fast on the spindle. The rotor has a hub engaging the spindle and extending for a predetermined axial distance. A rotor web extends radially from the hub and is axially shorter than the hub. Blades extend radially from the web and are axially longer than the web to leave annular cutaway portions on opposite sides of the rotor between the hub and the blades.

5 Claims, 2 Drawing Figures

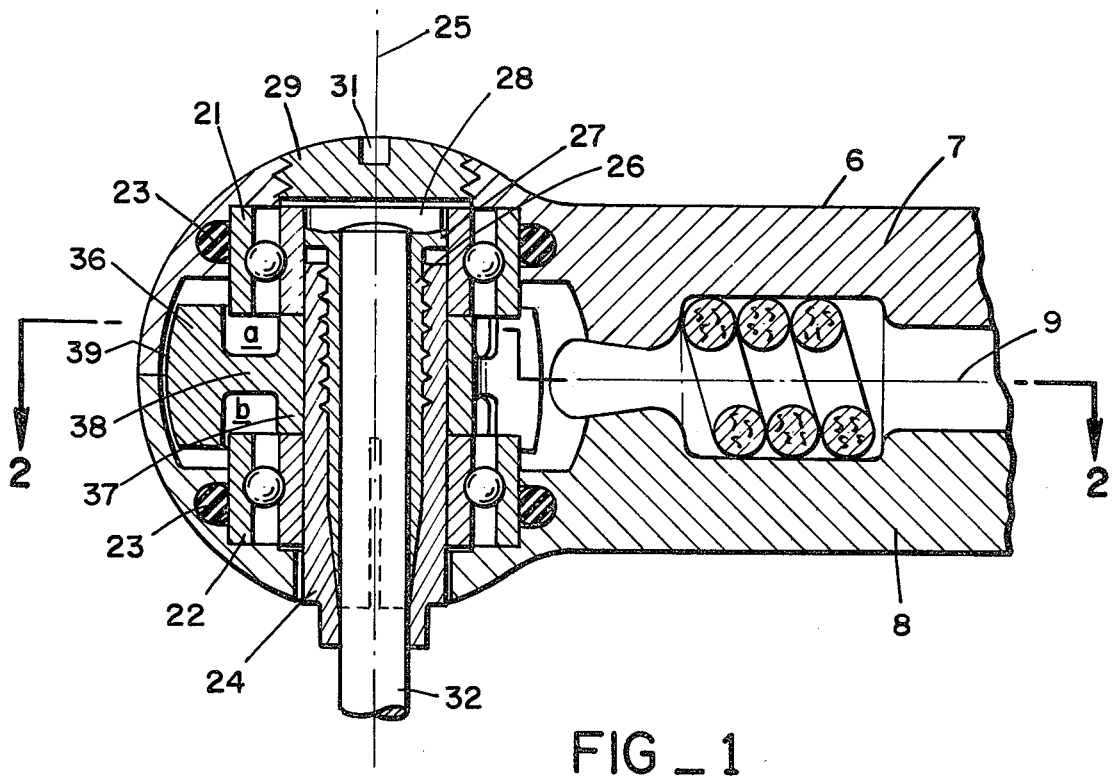
FIG_1
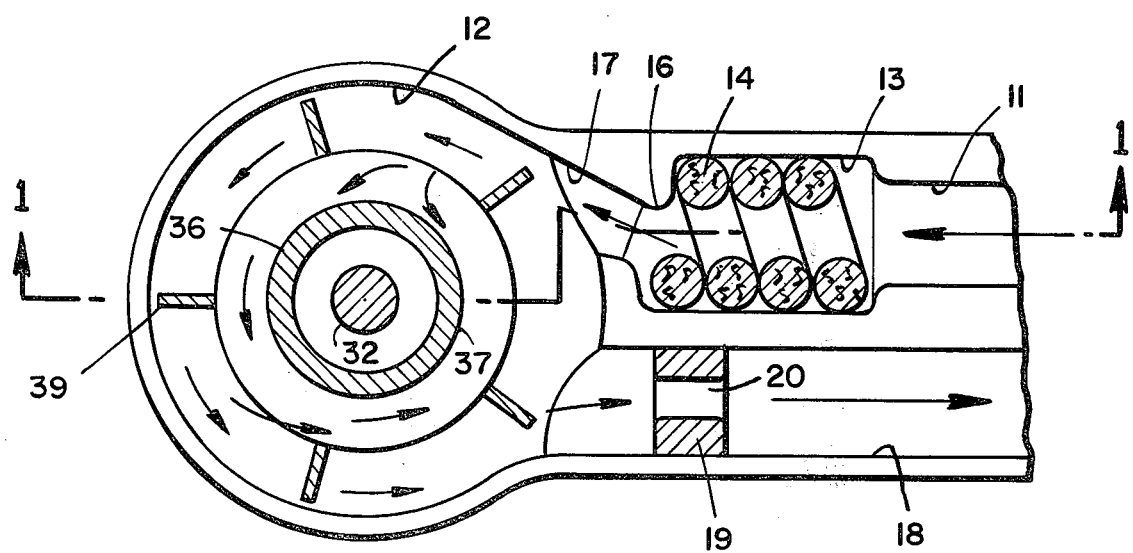
FIG_2

DENTAL HANDPIECE

A dental handpiece related to the present dental handpiece is disclosed in my co-pending application Ser. No. 301,263 filed Oct. 22, 1972, now Pat. No. 3,858,323, issued Jan. 7, 1975.

It is an object of this invention to provide a dental handpiece which is an improvement over dental handpieces in general and particularly is an advance over the handpiece set forth in the mentioned application.

Another object of the invention is to provide a dental handpiece driven by air and inclusive of a means for adding lubricant to the ingoing air.

Another object of the invention is to provide an air-operated dental handpiece in which means are provided for establishing a superatmospheric pressure within the interior of most of the handpiece.

Another object of the invention is to provide a dental handpiece driven by air and inclusive of a rotor having a configuration to facilitate the flow of air from the rotor to the air outlet.

An additional object of the invention is to provide a dental handpiece in which a housing encloses the operating parts but is constructed to afford easy access to the housing interior.

A still further object of the invention is to provide a dental handpiece in which the rotor is designed to reduce resonant vibration when used with the dental tools normally encountered.

A still further object of the invention is to provide an improved air turbine driven dental handpiece.

Other objects, together with the foregoing, are attained in the embodiment of the invention described in the accompanying description and illustrated in the accompanying drawings, in which:

FIG. 1 is a cross-section in axial and other planes through the handpiece of the invention; portions of the handpiece are broken away and the planes of section are indicated by the lines 1—1 of FIG. 2; and FIG. 2 is a cross-section of the handpiece shown in FIG. 1, the plane of section being indicated by the line 2—2 of FIG. 1.

In the present instance, the dental handpiece is of the air driven type disclosed in the mentioned application and includes a housing 6 preferably made up of an upper section 7 and a lower section 8. These are appropriately held together by suitable means, not shown, and abut on a common, central plane 9. The housing 6 is a generally solid body formed to provide an inlet duct 11 leading from an appropriate source of driving air under pressure and extending toward a circular, or partly spherical rotor chamber 12.

The duct 11 includes an enlarged wick compartment 13 designed to receive a coiled wick 14 or comparable body effective to carry a charge of lubricant, such as a light lubricating oil, in a position to be encountered by the incoming air. The air picks up lubricant to assist in the operation of the moving mechanism. The duct 11 beyond the compartment 13 is configured to provide an appropriately angled venturi throat portion 16 of a divergent nozzle 17.

Preferably, all of the duct 11 and the compartment 13 as well as the nozzle portions 16 and 17 are formed half in the upper portion 7 and half in the lower portion 8 of the housing. In this way rather complex configurations can be provided easily.

The divergent portion 17 of the nozzle opens into the rotor chamber 12 in a fashion to direct air tangentially to flow generally around the interior periphery of the housing.

In a comparable fashion there is also formed in the housing 6 an outlet duct 18 leading from the interior of the chamber 12 to a discharge point. The duct is preferably made of a relatively large diameter throughout most of its length but in accordance with the present arrangement carries a sleeve 19 providing a restricted orifice 20. The sleeve is firmly pressed into the outlet duct 18 and the restriction affords pressure higher than atmospheric within the chamber 12.

In the housing portions 7 and 8 are bearings 21 and 22 suitably supported in resilient O-rings 23 and carrying a spindle 24. This is rotatable in the bearings about an axis 25 normal to the plane 9 of division between the sections of the housing. The spindle 24 has a projecting, tool receiving end and is provided with a threaded and split interior sleeve 26 having a head 27 with a screwdriver slot 28 extending across it. The head 27 is normally enclosed but can be reached upon removal of a threaded plug 29 engaging threads in the body of the housing. The plug has a slot 31 for receiving a screwdriver or other tool. When the plug 29 is removed the sleeve 26 can be loosened or tightened with respect to the spindle in order to release or clamp the stem 32 of a dental tool such as a burr or the like. The customary dental tool has cutting teeth or blades evenly spaced around the axis and provided in an even number.

Particularly in accordance with this invention there is disposed between the bearings 21 and 22 and on and in driving engagement with the spindle 24 and symmetrical with the axis 25, an air turbine rotor 36. This is carefully balanced and so can be relatively heavy, preferably being made of gold alloy. The rotor has a central hub 37 having an axial extent sufficient closely to abut the bearings 21 and 22. The hub has a radial extent of a limited nature. Extending radially from the hub itself, either as a separate portion secured thereto or preferably integral therewith, is a central web 38. This is disposed symmetrically with the division plane 9 and extends axially for only a short distance substantially less than the predetermined axial extent of the hub.

Projecting radially from the web 38 is a plurality of blades or vanes 39. These are provided in any selected number but preferably the number selected is different from the number of blades on the central tool 32 and usually is an odd number. The number of blades does not correspond with the number of teeth on the central tool. The blades are of a radial extent sufficient to terminate very close to the spherical interior wall of the chamber 12 and have an axial extent at least as great as and sometimes greater than the predetermined axial extent of the hub 37. In this way the hub, the web and the interior of the various blades in effect define a pair of annular, rotor chambers a and b symmetrical with the central plane 9.

In the operation of this structure the incoming air under relatively high pressure is discharged, after picking up lubrication, from the nozzle 17 and flows approximately tangentially toward the receiving face of the next adjacent rotor vane. The vane faces are shown as radial but can be curved either convexly or concavely with respect to the air jet. The air jet is disturbed by encountering the vanes and becomes turbulent. It can then follow several paths for escape. One of the paths is with the vanes around the interior of the chamber 12 but is has been found in practice that air traveling in that fashion tends to obstruct the vanes and thus does not assist in high speed operation. Because of the provision of the annular chambers either side of the web 38, air can be deflected by turbulence or otherwise radially inwardly toward the axis 25 and is able to flow into the cutaway portions a and b. The used air can then flow around the hub and travel toward the outlet without interfering with the progress of the turbine vanes. The air can then flow outwardly in a generally radial and tangential direction into the outlet duct 18 and so through the restriction 20 and to the exhaust 18. Depending somewhat upon the contour of the blades or vanes, the once used air may, as it flows toward the outlet, again impinge upon the backs of the vanes with considerable force and impart a further rotary impulse to the rotor. Thus, considerable improvement in speed and power is made.

With the arrangement as described, the incoming air is lubricated, is discharged through a nozzle tangentially against the turbine rotor, impels the rotor at a high speed, escapes into the annular spaces either side of the web and then can escape from the interior of the rotor toward the outside. In most instances, depending somewhat upon blade configuration, the escaping air imparts a further driving impulse to the turbine. The restriction 20 is sufficient to maintain some back pressure in the housing since the only escape route other than the outlet is alongside the outside of the projecting spindle. Thus, the lubricant in the air is carried throughout the entire mechanism and escapes with a small fraction of the discharged impelling air and exterior debris is excluded from the mechanism.

It is found that the speed of operation of the turbine is much greater with the undercut rotor, a rotor defining the chambers a and b, than otherwise is the case. Also, since the number of rotor blades or vanes is different from the number of cutting edges on the customary burr or tool, the resonant frequency of rotational vibration, especially at higher speeds, is outside an objectionable range.

What is claimed is:

1. A dental handpiece comprising a housing defining a rotor chamber, an inlet duct leading through a nozzle opening into said chamber and an outlet duct opening from said chamber; a spindle mounted in said housing for rotation in said chamber about an axis; and a rotor in said chamber and mounted on said spindle, said rotor including an annular hub engaging and extending along said spindle for a predetermined axial distance, an annular web in a plane normal to said axis and extending radially from said hub and extending axially less than said distance, and circumferentially spaced axial blades extending radially from the outer edge of said web and extending an axial distance more than said web to leave rotor chambers on opposite sides of said web in communication with spaces between said blades.

2. A dental handpiece as in claim 1 in which said housing includes two portions abutting on a plane normal to said axis, said web lying on both sides of said plane and being substantially symmetrical therewith and establishing said rotor chambers substantially symmetrical therewith, and means each forming half of said inlet duct and said outlet duct in each of said portions and constituting said inlet duct and said outlet duct when said two portions are disposed in abutment with said means in each of said portions in registry.

3. A dental handpiece as in claim 1 in which said housing also defines an enlarged wick compartment in communication with said inlet duct, and a wick within said compartment.

4. A dental handpiece as in claim 1 including a sleeve defining a restricted orifice in said outlet duct.

5. A dental handpiece comprising a housing defining a substantially circular-cylindrical cavity having an axis, a pair of bearings in said housing and spaced apart along said axis, a turbine rotor in said cavity and having a hub disposed between and supported on said bearings, a plurality of axially and radially extending vanes spaced radially from said hub and circumferentially apart from each other around the periphery of said rotor to leave intervening spaces between said vanes, means in said housing defining an air inlet duct to said cavity and directed toward said vanes on one side of said axis, means in said housing defining an air outlet duct from said cavity and directed away from said vanes on the other side of said axis and lying alongside said inlet duct, and an axially thin annular web on said rotor of less axial extent than said vanes and said hub connecting said vanes and said hub and leaving annular chambers in said rotor on opposite sides of said web and in communication through said spaces between said vanes with said inlet duct and said outlet duct.

* * * * *